US012220320B2

(12) United States Patent
Sikora et al.

(10) Patent No.: US 12,220,320 B2
(45) Date of Patent: *Feb. 11, 2025

(54) IMPLANT AND ANCHOR ASSEMBLY

(71) Applicant: ARTHROSURFACE INCORPORATED, Franklin, MA (US)

(72) Inventors: George Sikora, Bridgewater, MA (US); Steven W. Ek, Bolton, MA (US)

(73) Assignee: ARTHROSURFACE INCORPORATED, Franklin, MA (US)

( * ) Notice: Subject to any disclaimer, the term of this patent is extended or adjusted under 35 U.S.C. 154(b) by 729 days.

This patent is subject to a terminal disclaimer.

(21) Appl. No.: 17/398,783

(22) Filed: Aug. 10, 2021

(65) Prior Publication Data

US 2022/0062000 A1    Mar. 3, 2022

Related U.S. Application Data

(63) Continuation of application No. 15/943,956, filed on Apr. 3, 2018, now Pat. No. 11,083,587, which is a continuation of application No. 14/640,529, filed on Mar. 6, 2015, now Pat. No. 9,931,219.

(60) Provisional application No. 61/950,762, filed on Mar. 10, 2014, provisional application No. 61/949,789, filed on Mar. 7, 2014, provisional application No. 61/949,824, filed on Mar. 7, 2014, provisional application No. 61/949,774, filed on Mar. 7, 2014.

(51) Int. Cl.
| | |
|---|---|
| *A61F 2/40* | (2006.01) |
| *A61B 17/064* | (2006.01) |
| *A61F 2/28* | (2006.01) |
| *A61F 2/30* | (2006.01) |
| *A61F 2/46* | (2006.01) |
| *A61B 17/04* | (2006.01) |

(52) U.S. Cl.
CPC ............ *A61F 2/40* (2013.01); *A61B 17/0642* (2013.01); *A61F 2/28* (2013.01); *A61F 2/30* (2013.01); *A61F 2/30756* (2013.01); *A61F 2/4081* (2013.01); *A61F 2/4606* (2013.01); *A61F 2/4618* (2013.01); *A61F 2/4637* (2013.01); *A61B 2017/0409* (2013.01); *A61B 2017/044* (2013.01); *A61B 2017/0648* (2013.01); *A61F 2002/30331* (2013.01); *A61F 2002/30364* (2013.01); *A61F 2002/30405* (2013.01); *A61F 2002/30462* (2013.01); *A61F 2002/305* (2013.01); *A61F 2002/30649* (2013.01); *A61F 2002/3085* (2013.01); *A61F 2002/4627* (2013.01); *A61F 2002/4628* (2013.01); *A61F 2310/00011* (2013.01)

(58) Field of Classification Search
CPC ............ A61F 2/30; A61F 2/40; A61F 2/4081
See application file for complete search history.

(56) References Cited

U.S. PATENT DOCUMENTS

2014/0194995 A1* 7/2014 Koka .................... A61F 2/4637
623/19.11

* cited by examiner

*Primary Examiner* — Brian A Dukert
(74) *Attorney, Agent, or Firm* — Grossman, Tucker, Perreault & Pfleger, PLLC

(57) ABSTRACT

An implant assembly comprising an implant having a load bearing surface with a contour corresponding to a patient's articular surface, and a bone facing surface including a fixation element, an anchor configured to be secured to bone beneath said patient's articular surface, said anchor including a second fixation element, and wherein said first fixation element is configured to be secured to said second fixation element.

20 Claims, 12 Drawing Sheets

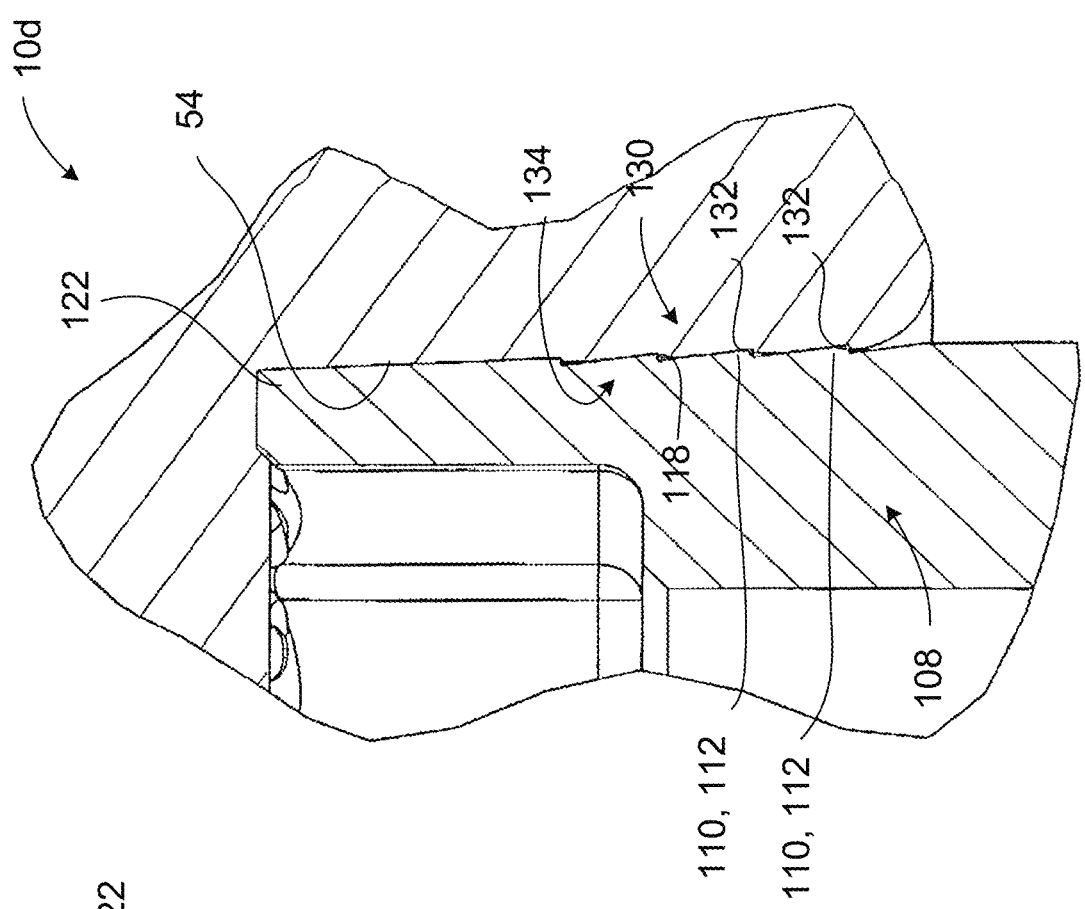
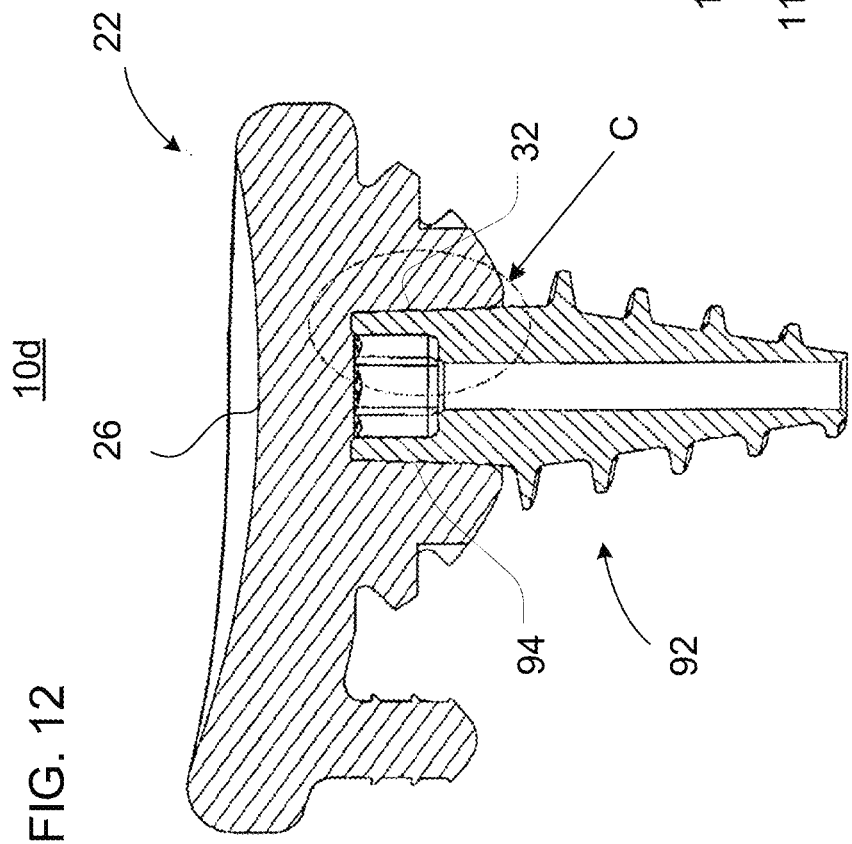
FIG. 12
FIG. 13

IMPLANT AND ANCHOR ASSEMBLY

CROSS REFERENCE TO RELATED APPLICATIONS

This application is a continuation of U.S. patent application Ser. No. 15/943,956 filed Apr. 2, 2018, which is a continuation of U.S. patent application Ser. No. 14/640,529 filed Mar. 6, 2015, now U.S. Pat. No. 9,931,219, which claims the benefit of U.S. Provisional Application Ser. No. 61/949,774, filed Mar. 7, 2014; U.S. Provisional Application Ser. No. 61/949,789, filed Mar. 7, 2014; U.S. Provisional Application Ser. No. 61/949,824, filed Mar. 7, 2014; and U.S. Provisional Application Ser. No. 61/950,762, filed Mar. 10, 2014, the entire disclosures of which are fully incorporated herein by reference.

FIELD

The present disclosure relates to devices and methods for the repair of defects that occur in cartilage on the surface of bone, as well as bone, particularly related to the human shoulder.

BACKGROUND

Articular cartilage, found at the ends of articulating bone in the body, is typically composed of hyaline cartilage, which has many unique properties that allow it to function effectively as a smooth and lubricious load-bearing surface. When injured, however, hyaline cartilage cells are not typically replaced by new hyaline cartilage cells. Healing is dependent upon the occurrence of bleeding from the underlying bone and formation of scar or reparative cartilage called fibrocartilage. While similar, fibrocartilage does not possess the same unique aspects of native hyaline cartilage and tends to be far less durable.

In certain instances, an injury may not be limited to the cartilage, but may also extend into the bone which supports the cartilage. For example, with a shoulder injury, such injury may include a fracture of the scapula and even more particularly a fracture of the glenoid rim to the glenoid cavity.

In some cases, it may be desirable or necessary to repair the damaged articular cartilage and/or bone using an implant. In instances where only cartilage may be damaged, the implant should have a shape substantially corresponding to the articular cartilage proximate the area where the implant is to be placed in order to maximize the patient's comfort, minimize damage to surrounding areas, and maximize the functional life of the implant. In instances where bone is damaged, the implant may be increased in size to accommodate the damaged location.

BRIEF DESCRIPTION OF THE DRAWINGS

Features and advantages of the claimed subject matter will be apparent from the following detailed description of some example embodiments consistent therewith, which description should be considered with reference to the accompanying drawings, wherein:

FIG. 12 is a cross-sectional side view of the anchor of FIGS. 8-11 assembled with an alternative implant body according to the present disclosure;

FIG. 13 is a close-up cross-sectional side view of the portion of the anchor and implant body of FIG. 12 bounded by circle C;

DETAILED DESCRIPTION

Figure 1:
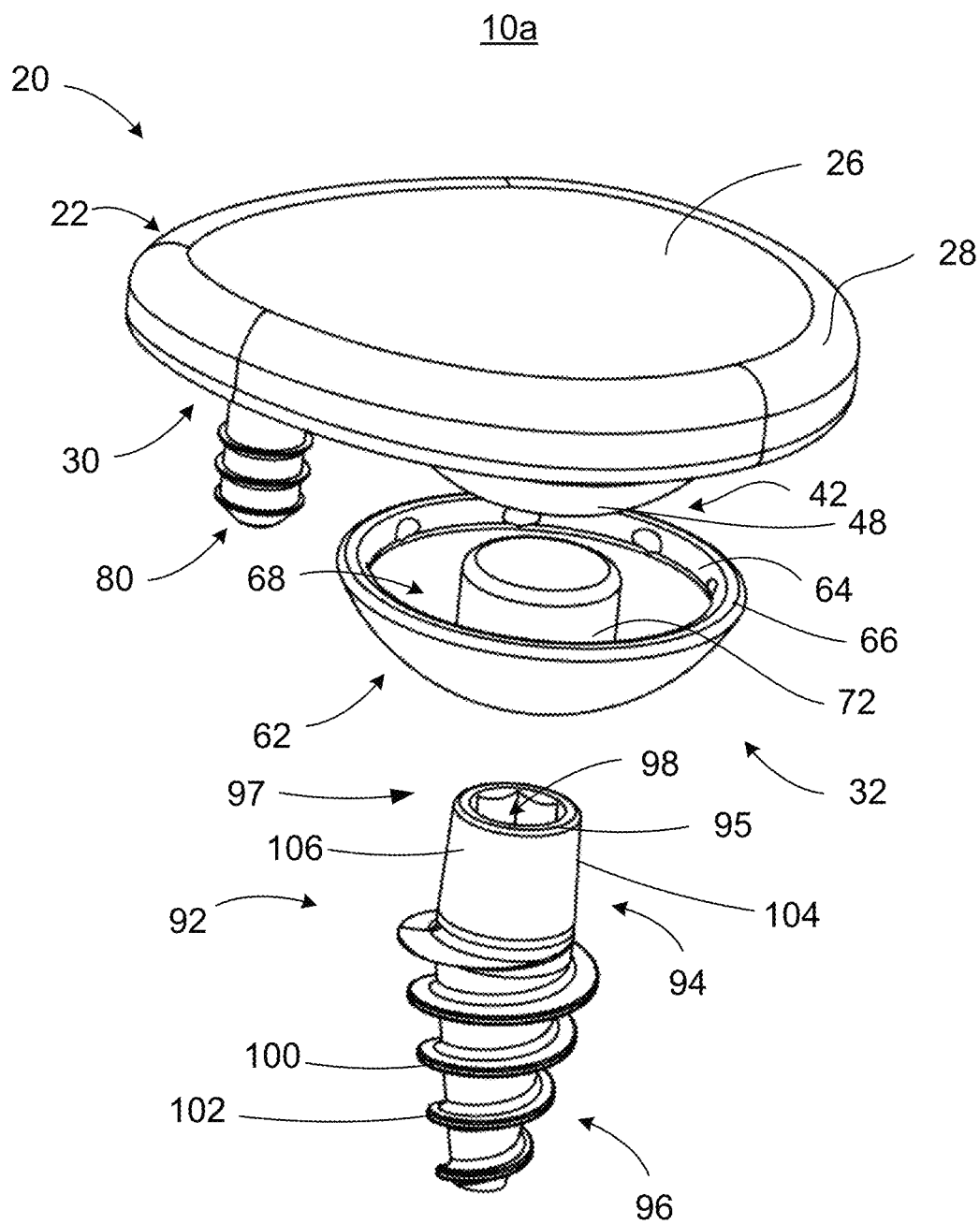
FIG. 1 is an exploded perspective view of a 3-piece implant assembly comprising an implant body, implant fixation member and an anchor according to one embodiment of the present disclosure.

Generally, the present disclosure may feature systems, devices, and method for forming an implant assembly. For example, the implant assembly may include an implant configured to be coupled to an elongated first anchor by way of a first and a second fixation element, respectively. The connection between the implant and the anchor may be configured to inhibit separation and/or rotation of the components relative to one another. The connection formed between the components may particularly be a frictional connection and/or a mechanical connection.

The implant and the anchor may be formed from different materials. For example, the implant may be formed of a plastic composition and/or a metal composition and the anchor may be formed of a plastic composition and/or a metal composition. In an embodiment in which the implant and the anchor are made from different materials, the implant may include an implant fixation member, which may be formed from a material the same as, or similar to, the material of the anchor. The implant fixation member may be secured to the implant body in a variety of ways include, but not limited to, snap fit connections, welding, overmolding, adhesives, and/or the like. The implant fixation member may include a first fixation element configured to form a connection with a second fixation element of the anchor to securely couple the implant to the anchor.

The implant assembly may be used to repair and/or replace any joint in the body. For example, the implant assemble may be used to repair and/or replace a synovial joint implant assembly such as, but not limited to, a balland-socket joint implant assembly including a shoulder joint implant assembly, particularly a glenoid implant assembly.

Mechanical connections formed between the components herein may include friction fit connections (which may also be referred to an interference or press fit) and positive mechanical engagement connections. A friction fit connection may be understood as a connection formed between the components which solely relies upon friction to inhibit separation of the components, particularly by one of the components being pressed into the other component such that at least one of the components is compressed (deformed) against one another. On the other hand, a positive mechanical engagement connection may be understood as a connection formed between the components which does not rely solely on friction to inhibit separation of the components and which includes a mechanical interlock to inhibit separation of the components (e.g. overlapping surfaces).

For the implant assemblies herein, in certain applications, a friction fit connection between the components may offer certain advantages over a positive mechanical engagement, such as where it is particularly desirable to inhibit rotation of the components relative to one another. In other applications, a positive mechanical engagement connection between the components may offer certain advantages over a friction fit connection, such as where it is particularly desirable to inhibit separation of the components relative to one another. In still other applications both a friction fit connection and a positive mechanical engagement connection may be particularly desirable to inhibit rotation and separation of the components relative to one another, respectively.

According to certain embodiments, the implant assembly may replace only a portion of the articular surface proximate the defect site rather than the entire articular surface. As such, the implant assembly may minimize the amount of the articular surface which is operated on thus allowing more of the patient's original articular surface to be unaffected and providing a more physiologically normal joint. However, in other embodiments, the implant assembly may replace the entire articular surface. In still other embodiments, the implant assembly may replace the portion of the bone adjacent (outside) the articular surface, such as the supporting rim of the joint, such as to repair, for example, a glenoid rim fracture.

Depending on the size of the implant assembly, such may allow for minimally invasive surgery, particularly arthroscopic surgery (which may also be referred to as keyhole surgery), which may reduce the amount of pain and/or discomfort experienced by the patient and may reduce healing times. However, while in certain embodiments the implant assembly may be configured to replace only a portion of the articular surface proximate the defect site rather than the entire articular surface, in other embodiments the implant assembly may be configured to replace the entire articular surface. For the sake of clarity, the bone and the excision site is generally not illustrated.

Figure 2:
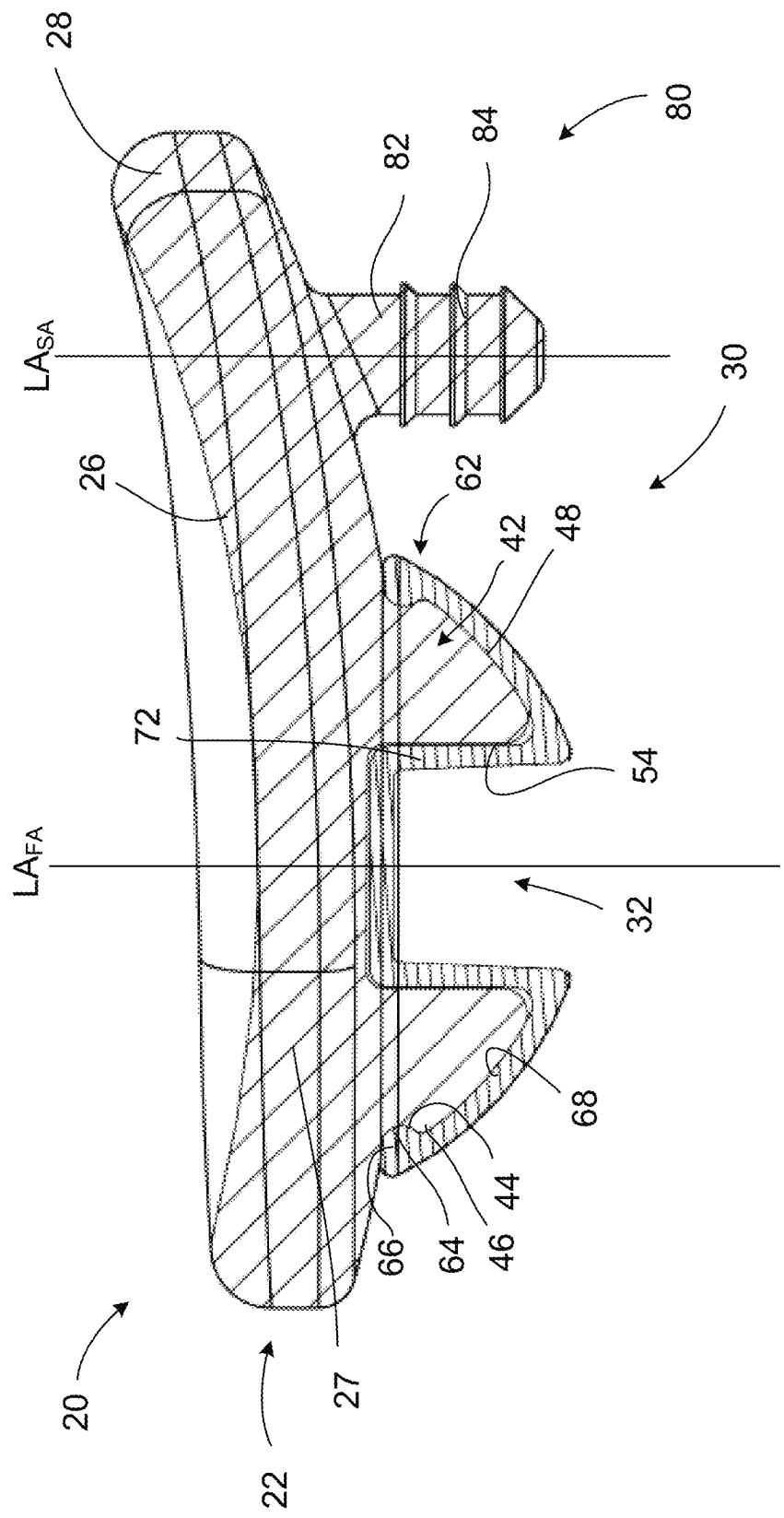
FIG. 2 is cross-sectional side view of the assembled implant body and implant fixation member of FIG. 1.
Figure 3:
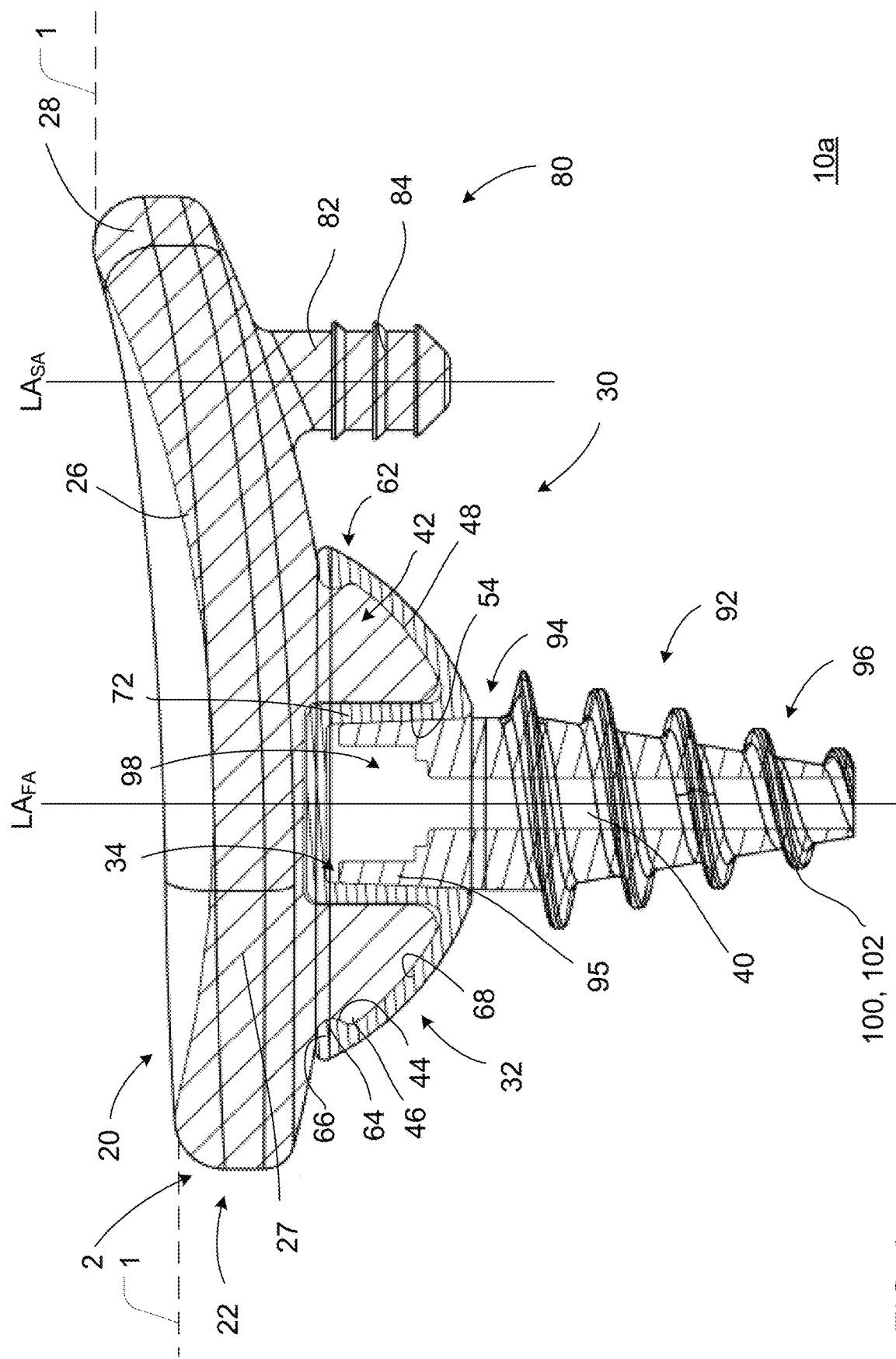
FIG. 3 is a cross-sectional side view of the assembled implant assembly of FIG. 1.

Referring now to FIGS. 1-3, there is shown an implant assembly 10a according to the present disclosure Implant assembly 10a comprises an implant 20 and an elongated first anchor 92. The implant 20 comprises an implant body 22 and an implant fixation member 62.

Implant body 22 may be formed of a plastic composition and may more particularly comprise, essentially consist of, or consist of a plastic composition. Exemplary plastic compositions may comprise thermoplastic compositions such as polyether ether ketone (PEEK) and polyethylene (PE), including ultrahigh molecular weight polyethylene (UHMWPE) and high density polyethylene (HDPE). In other embodiments, implant body 22 may be formed of a metal composition and may more particularly comprise, essentially consist of, or consist of a metal composition. Exemplary metal compositions may comprise stainless steel, titanium, aluminum, chromium cobalt, and/or any alloy thereof.

Implant 20, and more particularly implant body 22, has a joint facing side including a load bearing (joint articulation) surface 26, which is formed and supported by an articulation support region 27 (FIG. 2) of the implant body 22. The load bearing surface 26 may have a contour substantially corresponding to or based on the contour of an articular surface of a patient being repaired. The contour of the load bearing surface 26 may be based on a plurality of measurements taken at the patient's articular surface (for example, using a measuring and/or mapping tool as generally described in U.S. Pat. Nos. 6,520,964, 6,610,067, 6,679,917, 7,029,479 and 7,510,558, which are fully incorporated herein by reference) and/or may be based on one or more templates.

The load bearing surface 26 may be based on two or more curvatures, for example, the anterior-posterior curvature and the superior-inferior curvature. One or more of the anterior-posterior and/or superior-inferior curvatures may themselves be based on multiple curves, (for example, as generally described in U.S. patent application Ser. No. 12/027,121, filed Feb. 6, 2008 and entitled System and Method for Joint Resurface Repair, which is fully incorporated herein by reference). The load bearing surface 26 may be generally concaved. For example, the load bearing surface 26 may have a generally hemi-spherical shape. In certain embodiments, the load bearing surface 26 may be a generic (artificial) surface of the glenoid cavity.

The load bearing surface 26 may be surrounded by a beveled surrounding support region 28 disposed adjacent the perimeter of the load bearing surface 26. The beveled surrounding support region 28 may reduce the potential of further damage to the surrounding articular surface by eliminating a hard transition between the load bearing surface 26 and the remaining articular surface of the patient. The beveled region 28 may be particularly helpful if a portion of the implant assembly 10a is slightly proud with respect to the remaining articular surface.

The implant 20 also comprises a bone facing surface 30, which is shown to be non-planar and which may substantially correspond to a contour of an excision site formed in an articular surface of a patient. More particularly, a perimeter of the implant 20 may substantially corresponds to a perimeter of an excision site 2 formed in the articular surface 1 as generally illustrated in FIG. 3. The excision site 2 may be prepared, for example, as generally described in U.S. patent application Ser. No. 12/762,948, filed Febuary Apr. 19, 2010 and entitled Glenoid Resurfacing System and Method, which is fully incorporated herein by reference).

Implant 20 also includes a first fixation element 32 configured to engage with a second fixation element 94 (FIG. 1) of the elongated anchor 92 as generally illustrated in FIG. 3. In the illustrated embodiment, the first and the second fixation elements 32, 94 are illustrated as a tapered recess and a tapered protrusion configured to form a friction connection therebetween, but it should be appreciated that first fixation element 32 may be formed by a tapered protrusion and that the second fixation element 94 may be formed by a tapered recess. Examples of the first and second fixation elements 32, 94 are also described in U.S. Pat. Nos. 6,520,964, 6,610,067, 6,679,917, and 7,678,151, all of which are fully incorporated herein by reference. Alternatively, fixation elements 32, 94 may include, but are not limited to, snap-fits, press-fits, threads, or coupling elements.

In the illustrated embodiment, the first fixation element 32 is formed by the implant fixation member 62. The implant fixation member 62 may be secured to the implant body 22 in any manner known to those skilled in the art. For example, the implant body 22 may include one or more recesses 44 which extend continuously and/or partially (e.g., intermittently) round a circumference of an annular fixation ring 42 and the longitudinal axis of the first anchor $LA_{FA}$ in a direction which is oriented inward (i.e. transverse to a longitudinal axis of the first anchor $LA_{FA}$) as to create one or more undercuts and one or more corresponding lips 46, which also extend continuously and/or partially around a circumference of the annular fixation ring 42. As shown, with regards to the present embodiment, recess 44 is adjacent an intersection of the annular fixation ring 42 with the articulation support region 27 of the implant body 22, though this is not a limited of the present disclosure unless specifically claimed as such.

The implant fixation member 62 may include one or more fastener segments 64 configured to be received and generally correspond to the one or more recesses 44 of the implant body 22. The fastener segments 64 may be disposed about a perimeter circular edge 66 of the implant fixation member 62, for example, which abuts the articulation support region 27 of the implant body 22. During assembly of implant 20, the one or more fastener segments 64 of the implant fixation member 62 may be snap fit over the lip(s) 46 and into the recess(es) 44 of the implant body 22 to provide a positive mechanical engagement connection there between.

According to one embodiment, implant fixation member 62 and implant body 22 may be assembled by inserting annular fixation ring 42 of the implant body 22 into annular recess 68 of the implant fixation member 62. For example, implant fixation member 62 may line (e.g., cover and/or abut against) at least a portion of the sidewall 54 of annular fixation ring 42. More particularly, implant fixation member 62 may include a substantially cylindrical sidewall 72 (also tapered at a taper angle, for example, from 1 to 10 degrees) which is inserted into implant fixation recess 34 formed by annular fixation ring 42 of implant body 22. In order to increase the retention strength of implant fixation member 62 and implant body 22 to one another, the sidewall 72 of the implant fixation member 62 may form a friction fit connection against sidewall 54 defining implant fixation recess 34. The annular fixation ring 42 may include an arcuate leading end 48 which tapers with increasing distance away from articulation support region 27 and follows substantially the same contour as annular recess 68 of the implant fixation member 62. Thereafter, the one or more fastener segments 64 of the implant fixation member 62 may be snap fit over the lip 46 and into the recess 44 of the implant body 22 to provide the positive mechanical engagement connection there between.

While it has been described how implant fixation member 62 and implant body 22 may be secured to one another by mechanical connection (e.g., friction fit connection and/or positive mechanical engagement connection), implant fixation member 62 and implant body 22 may also be secured to one another by use of an adhesive (e.g. epoxy) there between, welding implant fixation member 62 and implant body 22 to one another, and/or insert injection molding implant fixation member 62 and implant body 22 to one another. For example, when implant fixation member 62 is formed of metal and implant body 22 is formed of plastic, the implant fixation member 62 may be inserted in an injection mold to form the implant body 22 and plastic to form the implant body 22 may be molded directly to the backside of the implant fixation member 62.

In certain embodiments, implant fixation member 62 may be formed of a plastic composition and may more particularly comprise, essentially consist of, or consist of a plastic composition. Exemplary plastic compositions may comprise thermoplastic compositions such as polyether ether ketone (PEEK) and polyethylene (PE) such as ultrahigh molecular weight polyethylene (UHMWPE) and high density polyethylene (HDPE). In other embodiments, implant fixation member 62 may be formed of a metal composition and may more particularly comprise, essentially consist of, or consist of a metal composition. Exemplary metal compositions may comprise stainless steel, titanium, aluminum, chromium cobalt, and/or any alloy thereof.

The first anchor 92, FIG. 3, is configured to be secured to the patient's bone 1 within the excision site 2 and includes a proximal end region 97 and a distal end region 96 as best illustrated in FIG. 1. As discussed herein, the proximal end region 97 includes a second fixation element 94 configured to be secured to the first fixation element 32 as illustrated in FIG. 3. As discussed herein, the second fixation element 94 may include a tapered protrusion. The tapered protrusion may include a sidewall 95 having an outer contour 104 which has a tapered, continuous substantially cylindrical surface 106 that substantially corresponds to the tapered surface of the first fixation element 32. In order to connect the first anchor 92 to the implant 20, the first and the second fixation elements 32, 94 may abut against each other to form a friction fit connection. For example, the substantially cylindrical surface 106 of the second fixation element 94 may contact the sidewall 72 of the first fixation element 32.

The first anchor 92 may comprise one or more anchor elements 100 configured to engage, connect, and/or secure the anchor 92 with the bone. For example, the anchor elements 100 may include one or more external screw (helical) threads 102 configured to threadably engage and connect with the bone. It should be appreciated, however, that one or more of the anchor elements 100 may include ribs, protrusions, barbs, or the like.

With reference to FIG. 1, proximal end region 97 of the first anchor 92 may include a driver receptacle 98 arranged to receive a drive member therein, particularly to drive the first anchor 92 into bone. Drive receptacle 98 may include any connection configured to transmit torque between a drive member including, but not limited to, a splined receptacle, a hex (single or double) drive receptacle, a square (single, double or triple) drive receptacle, a hexalobular drive receptacle, a polydrive (ribe) drive receptacle, a spline (four, six or twelve) drive receptacle and a pentalobular drive receptacle.

Elongated first anchor 92 may be formed of a plastic composition and may more particularly comprise, essentially consist of, or consist of a plastic composition. Exemplary plastic compositions may comprise thermoplastic compositions such as polyether ether ketone (PEEK) and polyethylene (PE) such as ultrahigh molecular weight polyethylene (UHMWPE) and high density polyethylene (HDPE). In other embodiments, first anchor 92 may be formed of a metal composition and may more particularly comprise, essentially consist of, or consist of a metal composition. Exemplary metal compositions may comprise stainless steel, titanium, aluminum, chromium cobalt, and/or any alloy thereof.

The bone facing surface 30 of implant 20 may further comprise a second elongated anchor 80, having a longitudinal axis $LA_{SA}$ which extends substantially parallel (within 5 degrees) with the first anchor longitudinal axis $LA_{FA}$. As shown, the second anchor 80 may have a cylindrical sidewall 82 with a plurality of barbs 84 which extend continuously around a circumference of the second anchor 80.

Implant assembly 10a may be assembled by first directly connecting implant fixation member 62 with implant body 22, and thereafter directing connecting first anchor 92 with implant 20 using the first and second fixation elements 32, 94. To install the implant assembly 10a into a patient's bone, an excision site is formed in the bone and first and second holes may be drilled into bone (e.g. scapula) to receive the first anchor 92 and the second anchor 80, respectively. The holes and/or the excision site may be drilled with one or more guides to ensure proper distance and orientation relative to one another. The implant assembly 10a may be implanted by first inserting the distal end anchor portion 96 of first anchor 92 into the first hole and rotating (or impacting) the first anchor 92 with a drive member to engage with and connect to the bone. Thereafter, the implant body 22 (with the implant fixation member 62 secured thereto) may be properly oriented and the first fixation element 32 of the implant fixation member 62 may be coupled to the second fixation element 94 of first anchor 92 to form a friction fit. The second anchor 80 may also be inserted in the second drilled bone hole and connected to the bone by a friction fit connection, particularly by barbs 84 pressing against the bone surface of the drilled hole.

Figure 4:
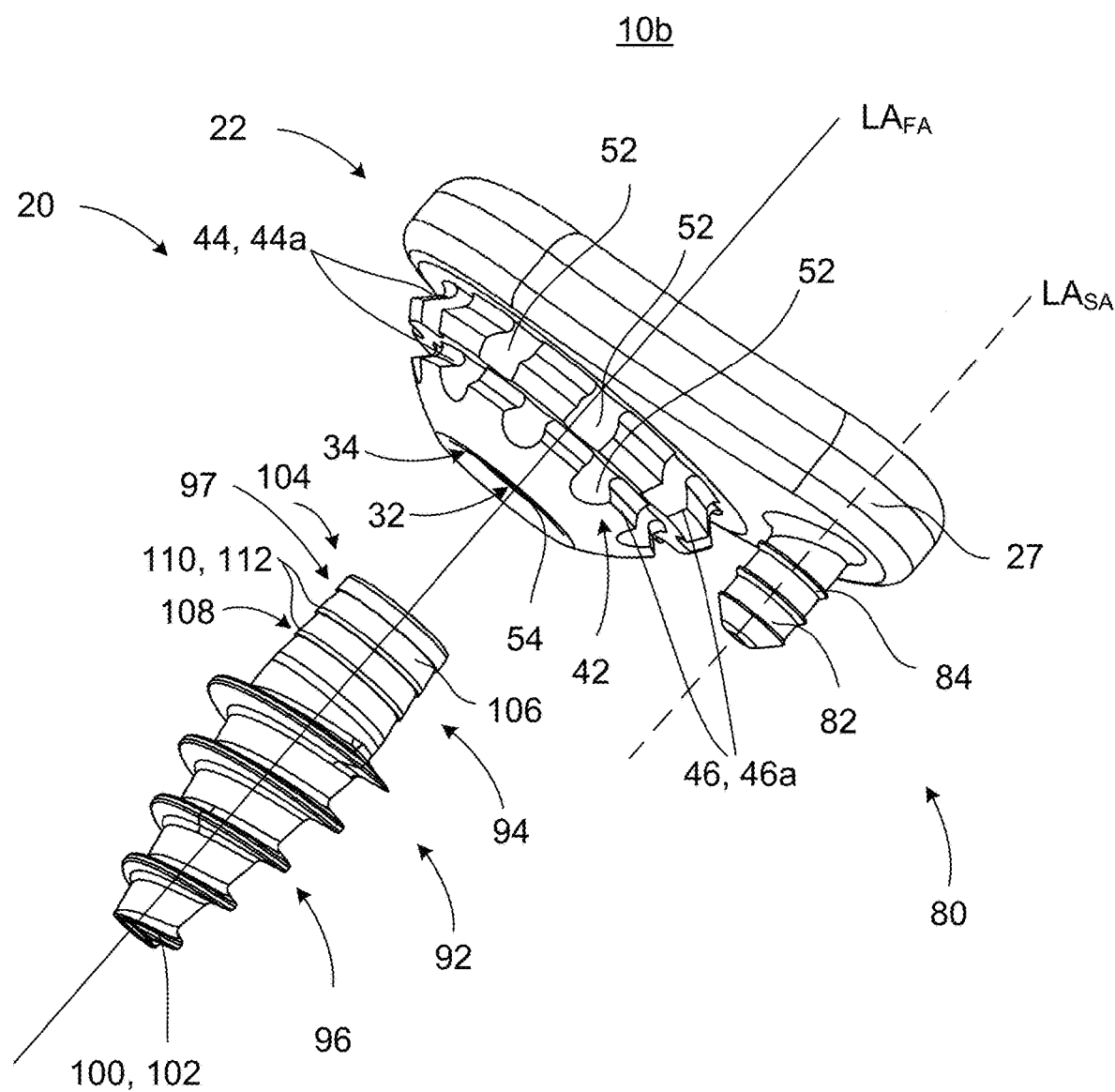
FIG. 4 is an exploded perspective view of a 2-piece implant assembly comprising an implant body and an anchor according to another embodiment of the present disclosure.

Referring now to FIG. 4, there is shown implant assembly 10b according to the present disclosure. In contrast to implant assembly 10a, implant assembly 10b eliminates implant fixation member 62. Furthermore, with regards to implant body 22, recess 44 and lip 46 of implant body 22 no longer extend continuously around the circumference of annular fixation ring 42, but rather extend intermittently around the circumference of the annular fixation ring 42. As shown, both the recess 44 and the lip 46 may be interrupted by a plurality of localized notches 52 which break the recess 44 and the lip 46 into a plurality of intermittent segments 44a and 46a, respectively which extend around a circumference of the annular fixation ring 42. With the elimination of implant fixation member 62, the recess 44 may provide pockets for bone growth or bone cement therein after the implant body 22 has been implanted to increase retention strength. Lip 46 may then inhibit the implant body 22 from being displaced (pulled) from the bone in the direction of the first anchor longitudinal axis $LA_{FA}$. The bone may also grow in (and/or the bone cement may flow into) notches 52, which will inhibit the implant body 22 from rotating around the first anchor longitudinal axis $LA_{FA}$.

As shown by FIG. 4, the outer contour 104 of second fixation element 94 may include at least one sidewall fixation feature 108. More particularly, sidewall fixation feature 108 may comprise at least one barb 110. As shown, the at least one barb 110 comprises a plurality of frusto-conical barb rings 112 which extend continuously around proximal end fixation element 94 and the first anchor longitudinal axis $LA_{FA}$.

In order to connect the first anchor 92 to implant body 22, the barbs 110, and more particularly the barb rings 112, may form a friction fit connection against sidewall 54 of the second fixation element 32 (e.g., the implant fixation recess 34) of implant body 22. The distal ends (e.g., tips) of the barb rings 112 may be arranged in an overall contour substantially corresponding to the taper of the first fixation element 32 (e.g., the taper of the sidewall 54 of the first fixation element 32. As such, the anchor 94 may be used with any first fixation element 32 having a corresponding taper. For example, a metal anchor 94 may be used with a plastic implant 20 and/or a metal implant 20 (e.g., metal implant fixation member 62). In the foregoing manner, the second fixation element 94 of first anchor 92 mechanically connects with the first fixation element 32 of the implant body 22.

Figure 6:
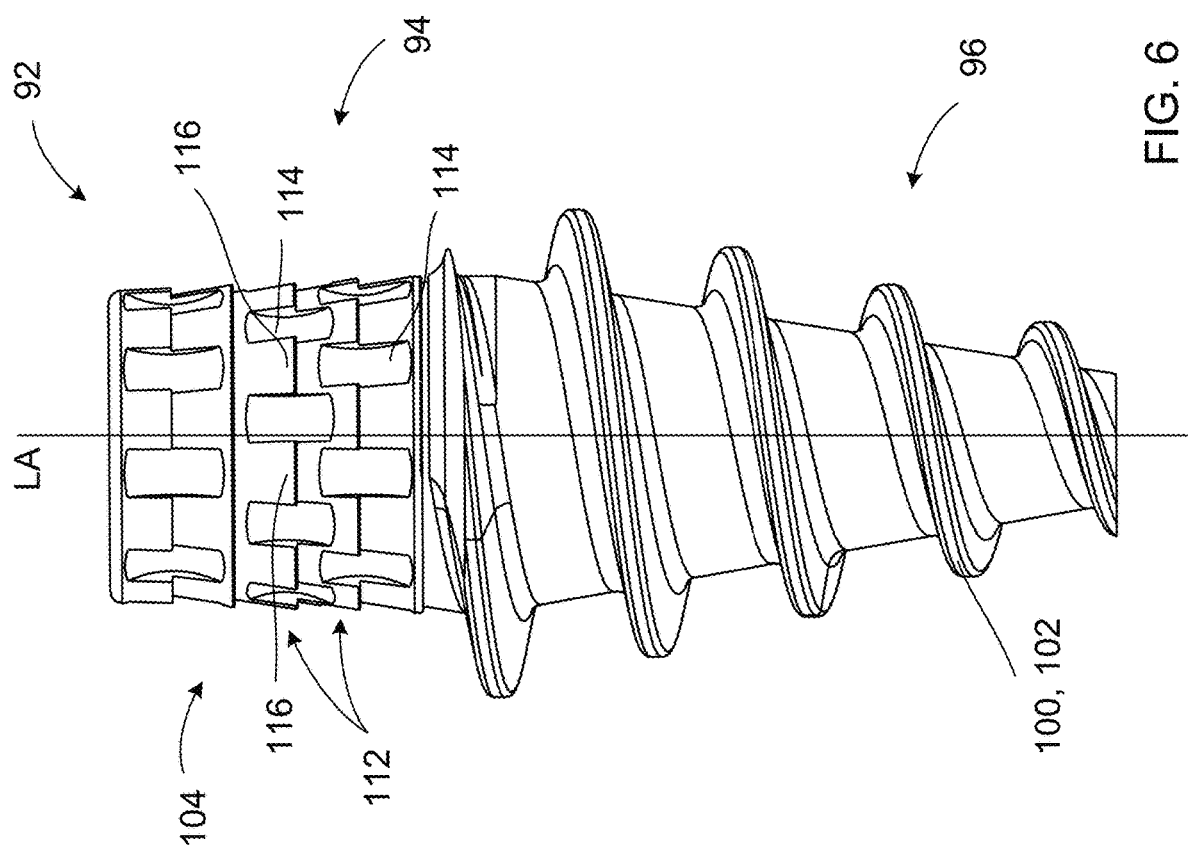
FIG. 6 is a side view of the anchor of FIG. 5.
Figure 5:
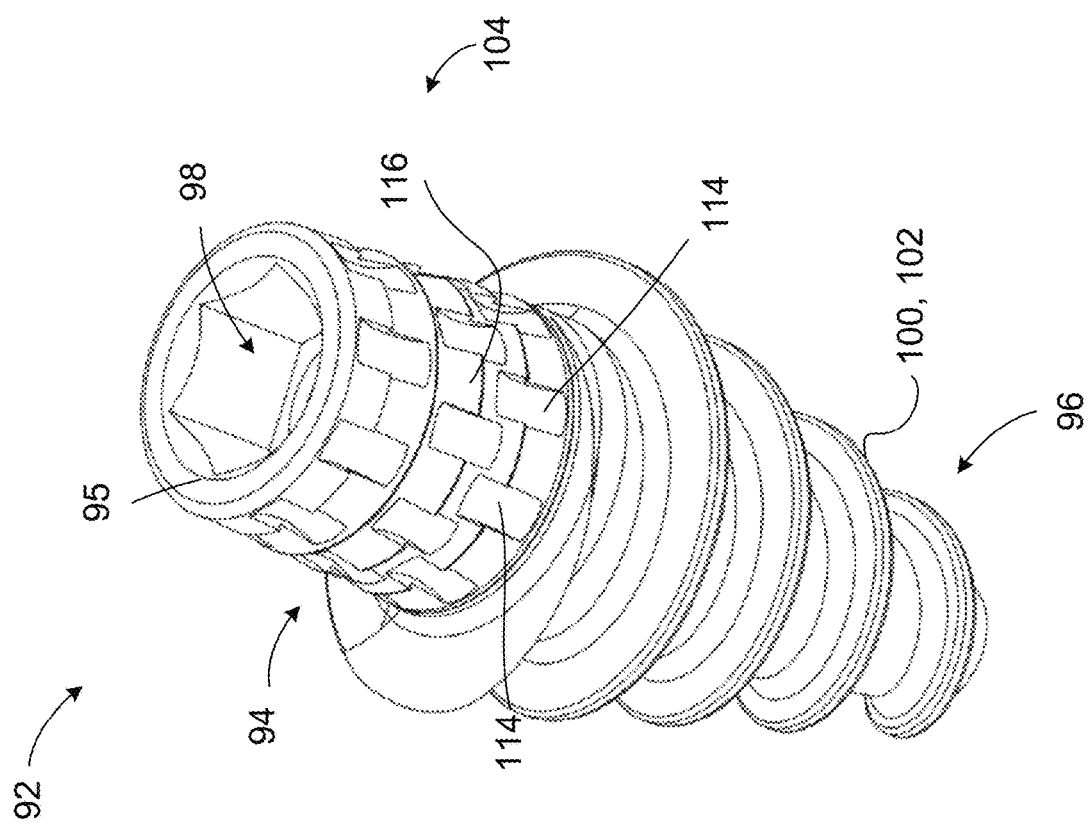
FIG. 5 is a perspective view of an alternative anchor according to the present disclosure.

Referring now to FIGS. 5-6, there is shown another embodiment of first anchor 92 according to the present disclosure. As shown, the outer contour 104 of proximal second fixation element 94 comprises a plurality of frusto-conical barb rings 112 which extend intermittently around second fixation element 94 and the first anchor longitudinal axis $LA_{FA}$. As shown, in contrast to the prior embodiment 10b, relief recesses 114 extend longitudinally through the barb rings 112 forming each barb ring 112 into a plurality of barb ring segments 116. Furthermore, as shown the barb ring segments 116 of each barb ring 112 are laterally offset to one another around the first anchor longitudinal axis $LA_{FA}$.

Figure 7:
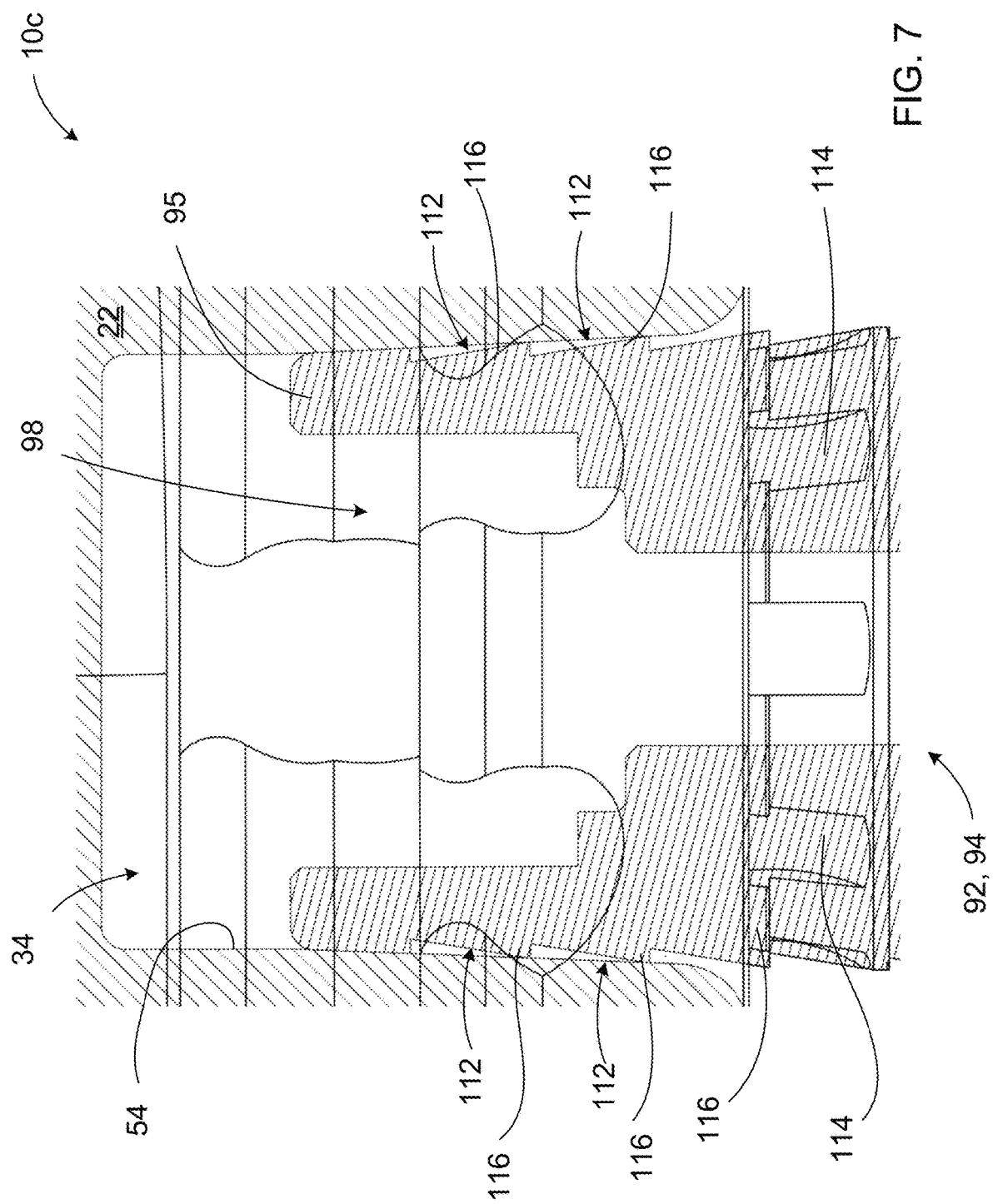
FIG. 7 is a cross-sectional side view of the anchor of FIGS. 5 and 6 assembled with the implant body of FIG. 4.

Referring now to FIG. 7, for implant assembly 10c, in order to connect the first anchor 92 to implant body 22, similar to the prior embodiment 10b, the barbs 110, and more particularly the barb rings 112, form a friction fit connection with the first fixation element 32 (e.g., against sidewall 54 of implant fixation recess 34 of implant body 22). For example, the barb ring segments 116 of the barb rings 112 form a friction fit connection against sidewall 54 of implant fixation recess 34 of implant body 22. In the foregoing manner, the second fixation element 94 of first anchor 92 mechanically connects with the implant body 22.

Referring now to FIGS. 8-11, there is shown another embodiment of a first anchor 92 according to the present disclosure. As shown, the outer contour 104 of second fixation element 94 comprises a plurality of frusto-conical barb rings 112 (FIG. 11) which extends continuously around proximal end fixation element 94 and the first anchor longitudinal axis $LA_{FA}$.

In addition, the outer contour 104 of second fixation element 94 comprises a second different sidewall fixation feature 108 in the form of a plurality of elongated ribs 122 (FIGS. 9 and 11) adjacent the plurality of frusto-conical barb rings 112, which are located between the frusto-conical barb rings 112 and a proximal end 120 of the first anchor 92. More particularly, the outer contour 104 of second fixation element 94 comprises a plurality of elongated ribs 122 separated by elongated relief recesses 124, both of which extend longitudinally with the longitudinal axis. Even more particularly, the plurality of elongated ribs 122 are substantially parallel (e.g., within 5 degrees) to one another and extend substantially parallel (e.g., within 5 degrees) along the first anchor longitudinal axis $LA_{FA}$.

Figure 9:
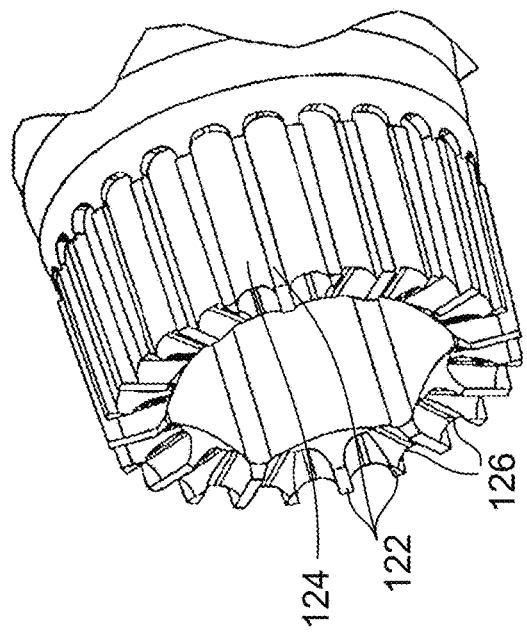
FIG. 9 a close-up perspective view of the portion of the anchor of FIG. 8 bounded by circle A.
Figure 10:
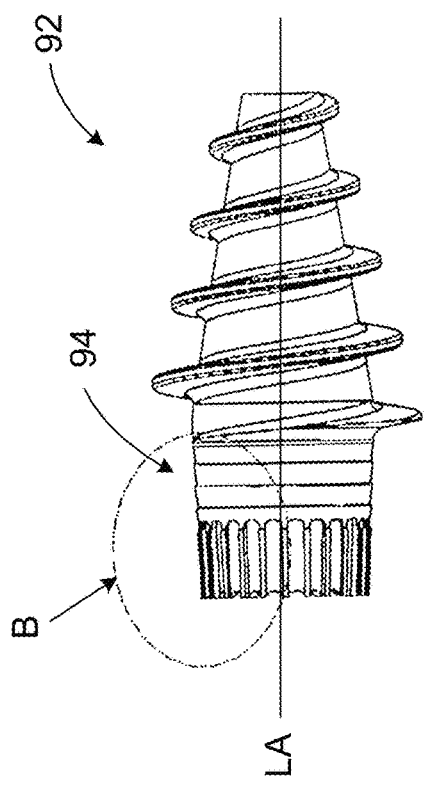
FIG. 10 is a side view of the anchor of FIG. 8.
Figure 8:
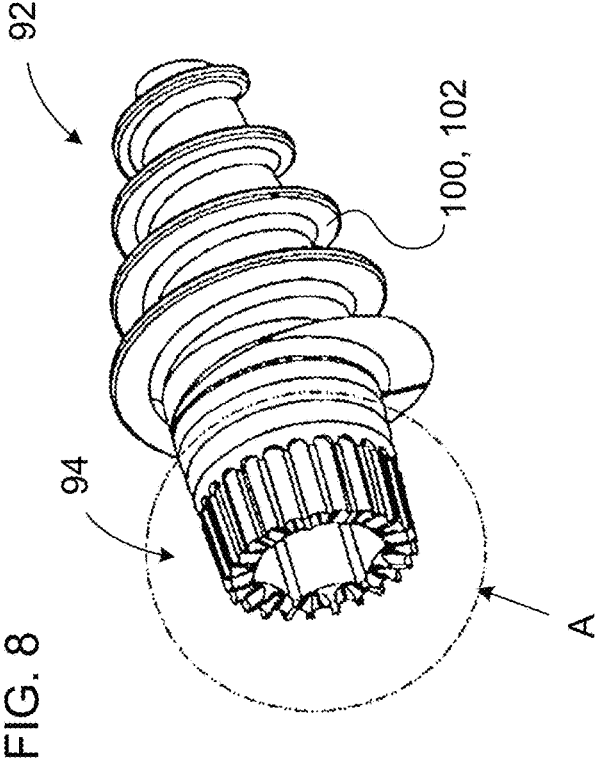
FIG. 8 is a perspective view of an alternative anchor according to the present disclosure.
Figure 11:
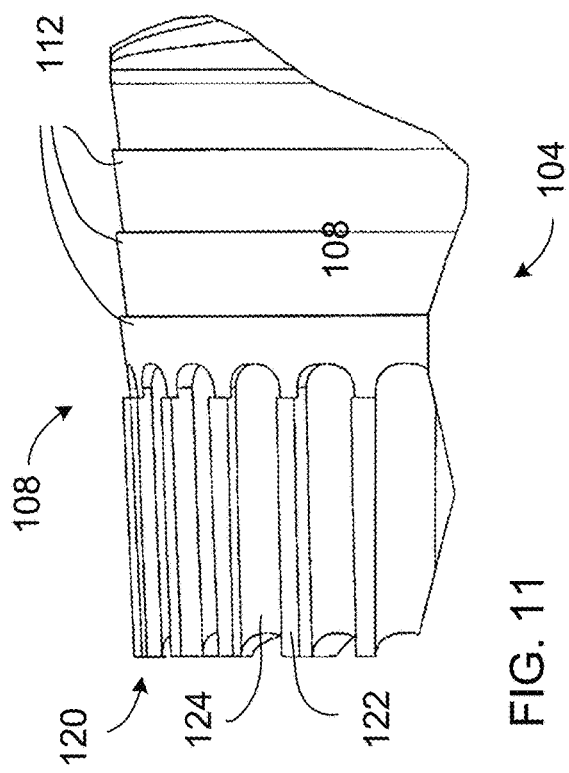
FIG. 11 is a close-up side view of the anchor of FIG. 10 bounded by circle B.

As best shown by FIG. 9, in addition to the elongated ribs 122 being arranged circumferentially around the outer contour 104 of the sidewall 95 of second fixation element 94, the plurality of ribs 122 may be arranged at the proximal end 120 of first anchor 92 which are separated by semi-circular recesses 126. In various embodiments, the present disclosure contemplates any number of elongated ribs 122. The elongated ribs 122 may be uniformly spaced from one another around the circumference of the second fixation element 94 of first anchor 92. Alternatively, the plurality of elongated ribs 122 may non-uniformly spaced from one another around the circumference of the second fixation element 94.

Referring now to FIGS. 12-13, for implant assembly 10d, in contrast to the prior embodiments 10a-10c, the first fixation element 32 (e.g., but not limited to, the implant fixation recess 34 of the implant body 22) includes at least one sidewall fixation feature 130 which is configured to mate and cooperate with the at least one sidewall fixation feature 108 of second fixation element 94 of first anchor 92 to form a positive mechanical engagement connection against separation of the implant body 22 from the first anchor 92.

More particularly, as shown, the at least one sidewall fixation feature 130 of the first fixation element 32 comprises an (undercut) ridge/step 132 in sidewall 54 of the implant fixation recess 34 which mates and cooperates with the ridge/step 118 of barb 110, and more particularly barb ring 112, to form the positive mechanical engagement. Even more particularly, the sidewall 54 of implant fixation recess 34, unlike prior embodiments 10a-10c, includes a frusto-conical surface 134 which mates and cooperates with frusto-conical barb ring 112. As such, the (undercut) ridge/step 132 in sidewall 54 of implant fixation recess 34 may be formed with a frusto-conical surface 134 which extends continuously around the sidewall 54 of implant fixation recess 34 and the first anchor longitudinal axis $LA_{F4}$. For example, the ribs 122 form a friction fit connection against sidewall portion 54 of implant fixation recess 34 of implant body 22 when the second fixation element 94 of first anchor 92 is fully inserted into implant fixation recess 34 of implant body 22. In addition, barb 110 and even more particularly barb ring 112, engages with the ridge/step 132 of the implant body 22 to form a positive mechanical engagement connection.

Specifically, the ridge/step 118 of barb 110, and more particularly barb ring 112, and the ridge/step 132 on the sidewall 54 of implant fixation recess 34 forms a mechanical interlock against separation of the implant body 22 from the first anchor 92. In the foregoing manner, the second fixation element 94 of first anchor 92 mechanically connects with the first fixation element 32 of the implant body 22, particularly by a friction fit connection and a positive mechanical engagement connection within implant fixation recess 34.

Figure 14:
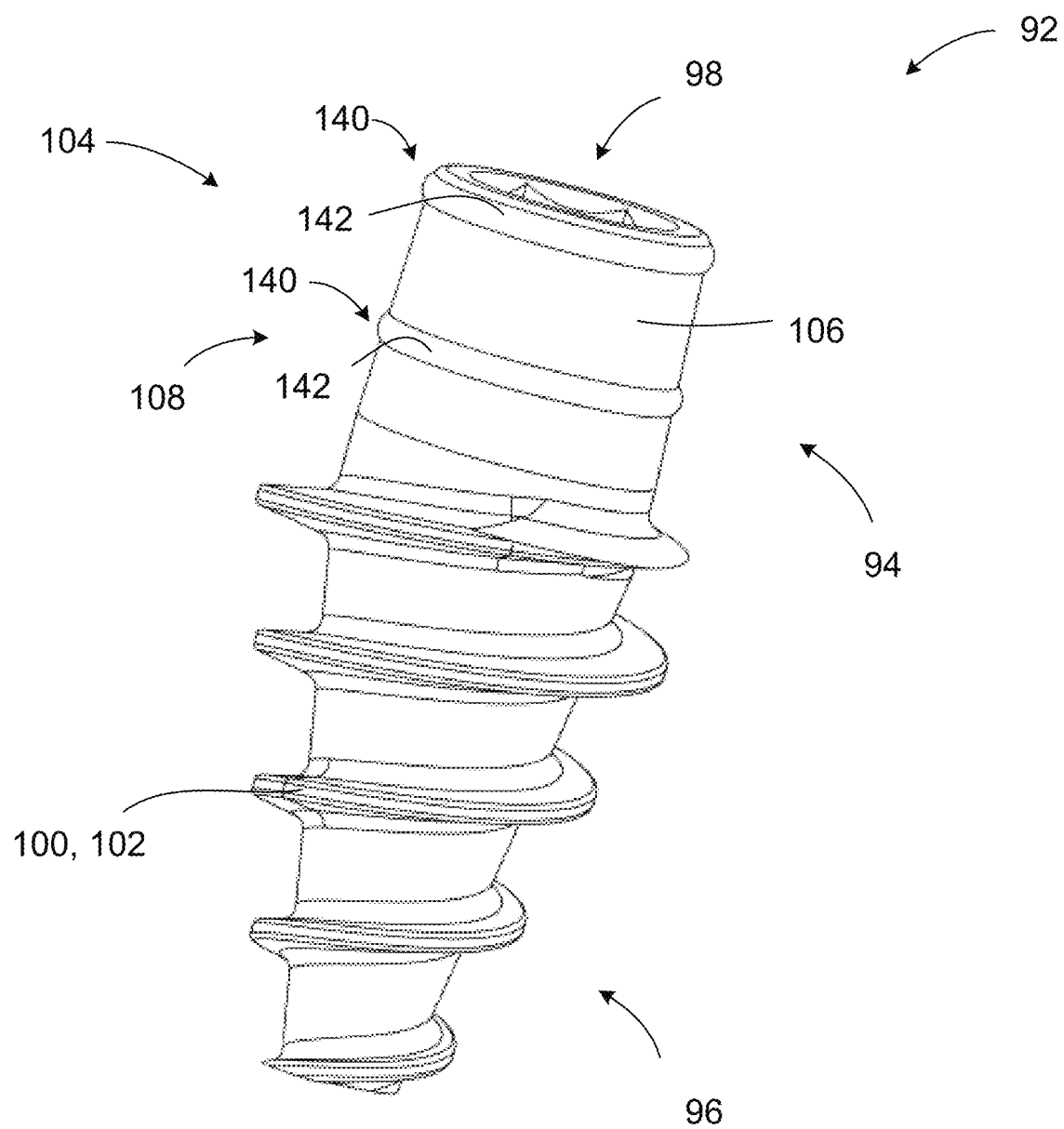
FIG. 14 is a is a perspective view of an alternative anchor according to the present disclosure.

Referring now to FIG. 14, there is shown another embodiment of a first anchor 92 according to the present disclosure. As shown, the outer contour 104 of second fixation element 94 comprises at least one sidewall fixation feature 108. More particularly, sidewall fixation feature 108 comprises at least one projection 140. The at least one projection 140 comprises a plurality of projections 140 which extend continuously and/or partially around second fixation element 94 and the first anchor longitudinal axis $LA_{F4}$. One or more of the projection 140 may have a semi-circular outer surface 142, though other cross-sections are possible.

Figure 15:
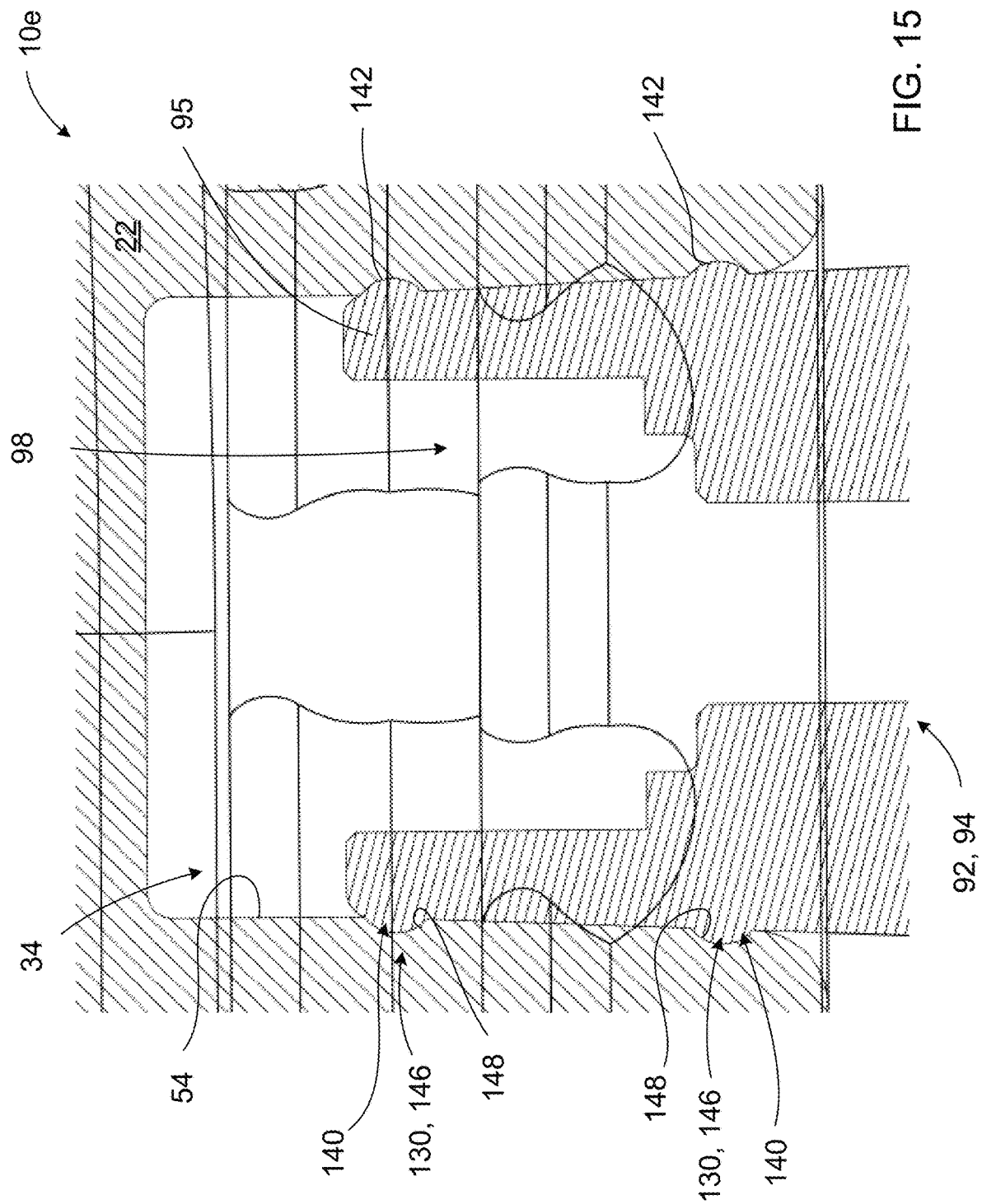
FIG. 15 is a cross-sectional side view of the anchor of FIG. 14 assembled with an alternative implant body according to the present disclosure.

Referring now to FIG. 15, another implant assembly 10e is generally illustrated. The first fixation element 32 (e.g., but not limited to, the implant fixation recess 34 of the implant body 22) includes at least one sidewall fixation feature 130 which is configured to mate and cooperate with the at least one sidewall fixation feature 108 of the second fixation element 94 of first anchor 92 to form a positive mechanical engagement connection against separation of the implant body 22 from the first anchor 92.

More particularly, as shown, the at least one sidewall fixation feature 130 of the first fixation element 32 comprises an (undercut) indentation 146 in sidewall 54 of implant fixation recess 34 which mates and cooperates with projection 140 to form the positive mechanical engagement connection. As such, the indentation 146 in sidewall 54 of first fixation element 32 may be formed with a semi-circular surface 148 which extends continuously and/or partially around the sidewall 54 of implant fixation recess 34 and the first anchor longitudinal axis $LA_{F4}$.

For implant assembly 10e, when the second fixation element 94 of first anchor 92 is fully inserted into first fixation element 32 of implant body 22, the sidewall fixation feature 108 of the second fixation element 94 (and more particularly projection 140) engages with the sidewall fixation feature 130 of the implant body 22 (and more particularly indentation 146) to form a positive mechanical engagement connection.

Unlike the prior embodiments, in which the second fixation element 94 of first anchor 92 mechanically connects with the first fixation element 32 particularly by a friction fit connection, with the present embodiment the second fixation element 94 of first anchor 92 may mechanically connect with the first fixation element 32 solely by a positive mechanical engagement connection within implant fixation recess 34 of the implant body 22.

Figure 16:
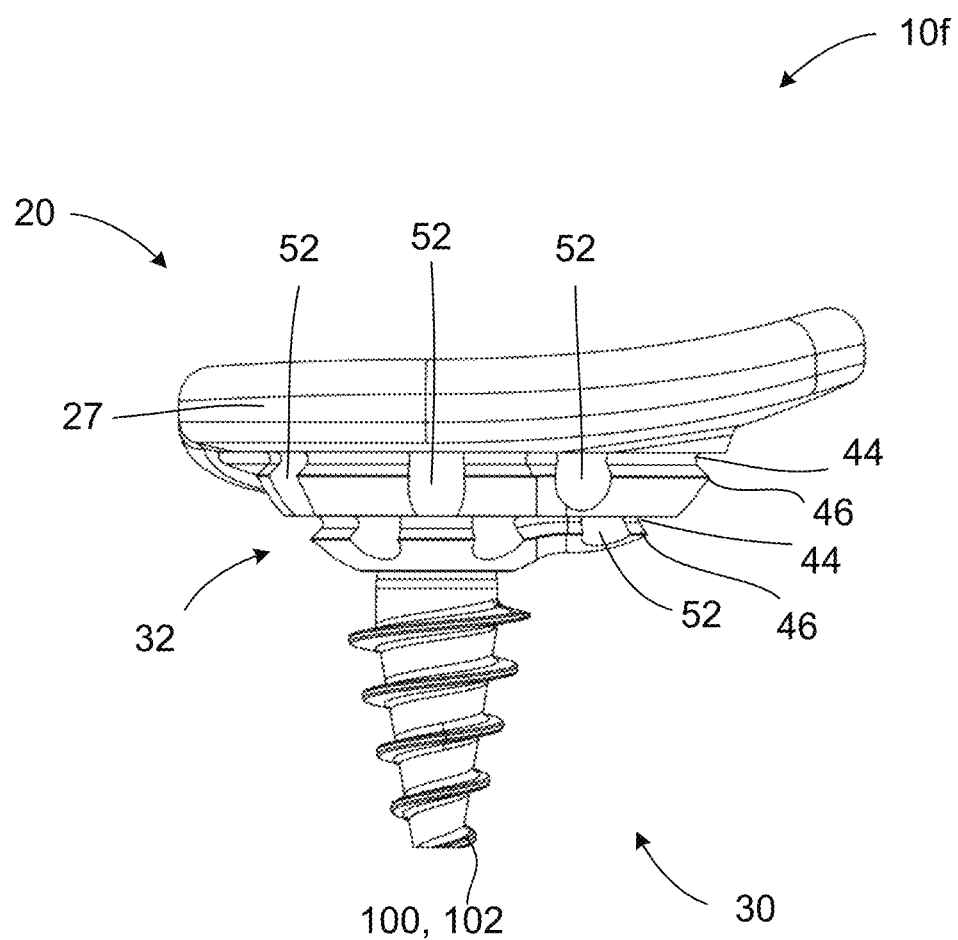
FIG. 16 is a side view of another two-piece implant assembly according to another embodiment of the present disclosure.

Referring now to FIG. 16, it may be appreciated that any embodiment of an implant assembly consistent with the present disclosure may eliminate the second elongated anchor 80.

Figure 17:
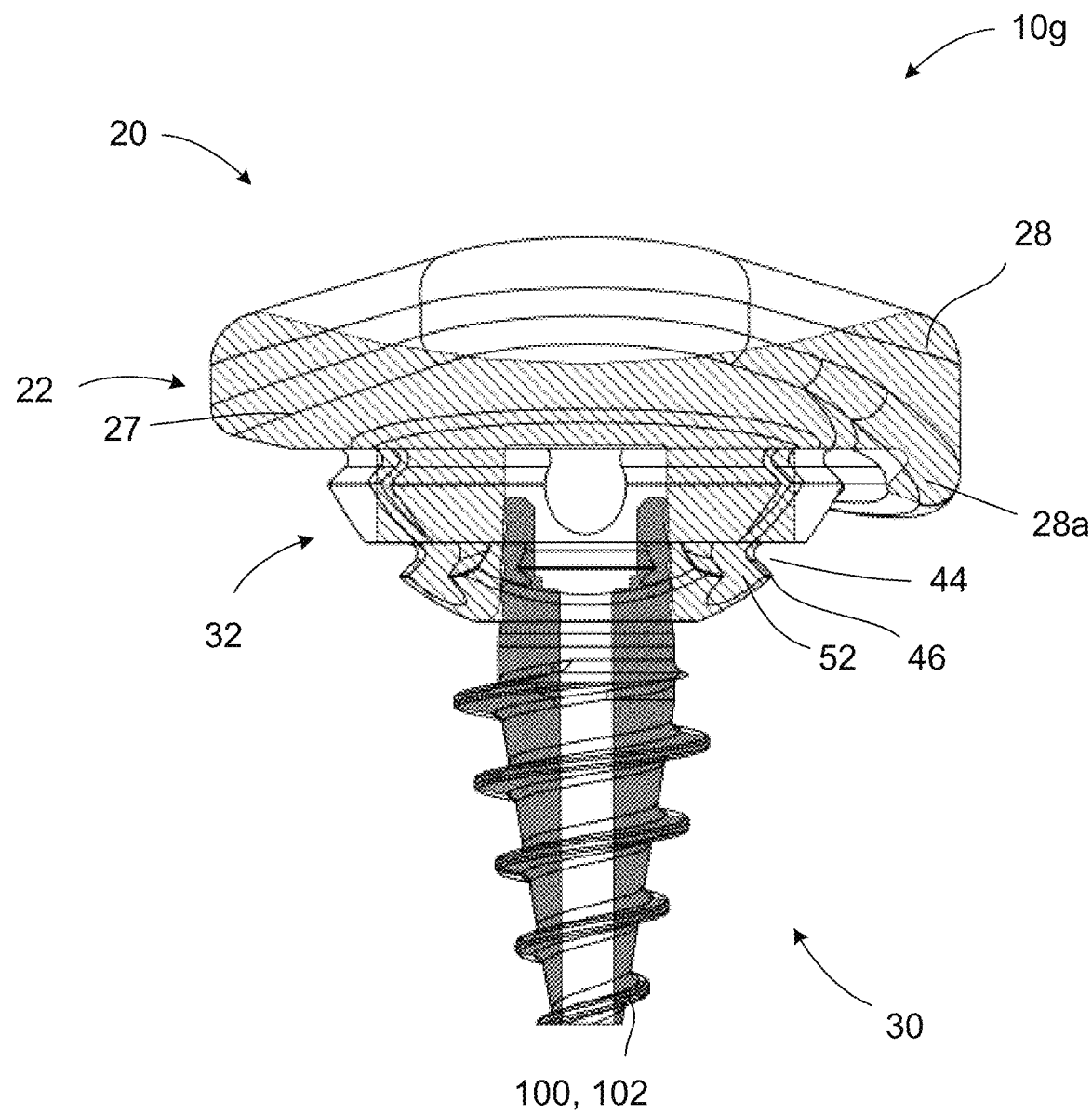
FIG. 17 is a cross-sectional side view of an implant assembly comprising an implant body and an anchor according to another embodiment of the present disclosure.

Referring now to FIG. 17, for implant assembly 10g the beveled surrounding support region 28 of the implant body 22 disposed adjacent articulation support region 27 and the perimeter of the load bearing surface 26 may be thickened in local areas 28a relative to other adjacent areas of the implant body 22 and support region 28 to provide localized support for a glenoid rim fracture, particularly where a portion of the glenoid rim may be actually broken off from the scapula, such as may occur with an anterior or posterior dislocation. In such instance, support region 28 the implant body 22 may be thickened localized areas 28a which correspond to anterior and/or posterior glenoid rim fractures.

As noted herein, the first and the second fixation elements 32, 94 forming the connection between the implant 20 and the anchor 94 may be reversed. In other words, the first fixation element 32 of the implant 20 (which is generally illustrated in the figures as comprising a tapered recess 34) may be formed as a tapered protrusion, while the second fixation element 94 of anchor 92 (which is generally illustrated as a tapered protrusion) may be formed as a tapered recess.

It should also be appreciated that any embodiment of the first and/or second fixation elements 32, 94 may have an overall contour (including any barbs, undercuts, or the like) which substantially correspond to each other. As such, a single anchor 92 consistent with the present disclosure may be used (with and form a secure connection with) any implant 20 described herein, and any implant 20 consistent with the present disclosure may be used with (and form a secure connection with) any anchor described herein.

Any embodiment of the anchor 94 disclosed herein may optionally include a cannulated passageway 40, for example as generally illustrated in FIG. 3. The cannulated passageway 40 may be configured to be advanced over a guide wire (not shown) extending outwardly from the excision site in the bone as generally described in U.S. Pat. Nos. 6,520,964, 6,610,067, 6,679,917, and 7,678,151, all of which are fully incorporated herein by reference. The use of a cannulated passageway 40 and the guide wire may facilitate alignment of the anchor 30 with respect to the excision site and the surrounding articular surface.

According to one aspect, the present disclosure may feature an implant assembly comprising an implant and an anchor. The implant may have a load bearing surface with a contour corresponding to a patient's articular surface, and a bone facing surface including a first fixation element. The anchor may be configured to be secured to bone beneath the patient's articular surface, and may include a second fixation element. The first fixation element is configured to be secured to the second fixation element.

It may be appreciated that the present disclosure is not limited in its application to the details of construction and the arrangement of components set forth in the following description or illustrated in the drawings. The invention(s) herein may be capable of other embodiments and of being practiced or being carried out in various ways. Also, it may be appreciated that the phraseology and terminology used herein is for the purpose of description and should not be regarded as limiting as such may be understood by one of skill in the art.

Throughout the present description, like reference numerals and letters indicate corresponding structure throughout the several views, and such corresponding structure need not be separately discussed. Furthermore, any particular feature(s) of a particular exemplary embodiment may be equally applied to any other exemplary embodiment(s) of this disclosure as suitable. In other words, features between the various exemplary embodiments described herein are interchangeable as suitable, and not exclusive.

While a preferred embodiment of the present invention(s) has been described, it should be understood that various changes, adaptations and modifications can be made therein without departing from the spirit of the invention(s) and the scope of the appended claims. The scope of the invention(s) should, therefore, be determined not with reference to the above description, but instead should be determined with reference to the appended claims along with their full scope of equivalents. Furthermore, it should be understood that the appended claims do not necessarily comprise the broadest scope of the invention(s) which the applicant is entitled to claim, or the only manner(s) in which the invention(s) may be claimed, or that all recited features are necessary.

What is claimed is:

1. An implant assembly comprising:
   an implant having a load bearing surface with a contour corresponding to a patient's articular surface, and a bone facing surface including a first fixation element;
   an anchor configured to be secured to bone beneath said patient's articular surface, said anchor including a second fixation element; and
   wherein said first fixation element is configured to be secured to said second fixation element;
   wherein said first fixation element and said second fixation element are configured to mechanically connect with each other to form a mechanical connection therebetween, said first fixation element and said second fixation element are further configured to frictionally engage with each other to form a frictional connection therebetween;
   one of said first fixation element and said second fixation element comprises a protrusion comprising a protrusion sidewall having an exterior surface, an interior surface defining a cavity, and a thickness extending therebetween;
   said protrusion sidewall includes at least one protrusion sidewall fixation feature, said at least one protrusion sidewall fixation feature comprises a plurality of ribs and at least one plurality of relief recesses extending through the exterior surface of the protrusion sidewall to a non-zero distance from the interior surface of the protrusion sidewall, and wherein the plurality of ribs are separated by the plurality of relief recesses.

2. The implant assembly of claim 1, wherein:
   said at least one relief recesses extends longitudinally along a longitudinal length of said protrusion.

3. The implant assembly of claim 1, wherein:
   said plurality of ribs are substantially equally spaced around a circumference of said protrusion.

4. The implant assembly of claim 1, wherein:
   said plurality of ribs are substantially parallel to each other.

5. The implant assembly of claim 1, wherein:
   said implant comprises plastic; and
   said first fixation element and said second fixation element each comprise metal.

6. The implant assembly of claim 1, wherein:
   said implant comprises metal; and
   said first fixation element and said second fixation element each comprise plastic.

7. The implant assembly of claim 1, wherein:
   said first fixation element and said second fixation element are further configured to mechanically interlock with each other to form a positive mechanical engagement therebetween.

8. The implant assembly of claim 7, wherein:
   said first fixation element comprises a tapered recess; and
   said second fixation element comprises a tapered protrusion.

9. The implant assembly of claim 7, wherein:
   said first fixation element comprises a tapered protrusion; and
   said second fixation element comprises a tapered recess.

10. The implant assembly of claim 7, wherein:
    one of said first fixation element or said second fixation element comprises a protrusion having a protrusion sidewall; and
    said protrusion sidewall includes at least one protrusion sidewall fixation feature;
    and said other of said first fixation element or said second fixation element comprises a recess having a recess sidewall; and
    said recess sidewall includes at least one recess sidewall retention feature.

11. The implant assembly of claim 10, wherein:
    said at least one protrusion sidewall fixation feature is configured to mate with said at least one recess sidewall fixation feature to form said mechanical interlock.

12. The implant assembly of claim 10, wherein:
    said at least one protrusion sidewall fixation feature comprises at least one barb;
    said at least one recess sidewall fixation feature comprises at least one ridge; and
    said at least one barb is configured to cooperate with said at least one ridge to form said mechanical interlock.

13. The implant assembly of claim 10, wherein:
    said at least one protrusion sidewall fixation feature comprises at least one projection; and
    said at least one recess sidewall fixation feature comprises at least one indentation;
    and said at least one projection is configured to mate with said at least one indentation to form said mechanical interlock.

14. The implant assembly of claim 1, wherein:
    said first fixation element is formed by an implant body and an implant fixation member.

15. The implant assembly of claim 14, wherein:
    said implant body and said implant fixation member are secured to one another by at least one of a friction fit connection, a positive mechanical engagement connection and an adhesive connection.

16. The implant assembly of claim 1, wherein:
at least a portion of said anchor includes a threaded portion configured to engage said bone.

17. The implant assembly of claim 1, wherein:
said implant is a synovial joint implant, a ball and socket joint implant or a shoulder joint implant.

18. The implant assembly of claim 1, wherein:
said at least one protrusion sidewall fixation feature comprises at least one barb.

19. The implant assembly of claim 18, wherein:
said at least one barb forms a ring extending continuously around said circumference of said protrusion.

20. The implant assembly of claim 18, wherein said at least one barb forms a ring comprising a plurality of barb ring segments which extend around said circumference of said protrusion.

* * * * *